United States Patent [19]

Miller et al.

[11] Patent Number: 5,270,058

[45] Date of Patent: Dec. 14, 1993

[54] ALDEHYDE SULFOXYLATE SYSTEMIC FUNGICIDES

[75] Inventors: Jorge Miller; Alberto Kling, both of Bogota, Colombia

[73] Assignee: Mauricio Kling, Munich, Fed. Rep. of Germany

[21] Appl. No.: 950,501

[22] Filed: Sep. 25, 1992

[51] Int. Cl.⁵ .................. A01N 59/20; A01N 37/02; A01N 35/02; A01N 31/02
[52] U.S. Cl. .................. 424/638; 514/578; 514/694; 514/702; 514/707; 514/709; 514/711
[58] Field of Search ............... 514/578, 694, 702, 707, 514/709, 711; 424/638

[56] References Cited

U.S. PATENT DOCUMENTS 3,039,959   6/1962   Hughes ........................... 514/578

OTHER PUBLICATIONS

The Merck Index, 10th Edition, Windholz (editor), Merck & Co., Rahway NJ, 1983 pp. 1235, 1236, 379-380.
Grant & Hackh's Chemical Dictionary, 5th Edition, Grant et al (editor), McGraw Hill, NY, 1987, p. 509.

*Primary Examiner*—Allen J. Robinson
*Assistant Examiner*—B. Bembenick
*Attorney, Agent, or Firm*—Jacobson, Price, Holman & Stern

[57] ABSTRACT

An alkali-metal dithionite is readily transformed into an aldehyde sulfoxylate microbicide which is absorbed through plant leaves and is more stable against oxidation.

9 Claims, No Drawings

5,270,058

ALDEHYDE SULFOXYLATE SYSTEMIC FUNGICIDES

FIELD OF THE INVENTION

Aldehyde sulfoxylates systemic fungicides which are absorbable through leaves of plants.

BACKGROUND OF THE INVENTION

Sodium dithionate is an effective microbicide and it is used as a food additive classified as GRAS (generally recognized as safe) Federal Reg. 06117 (Jan. 25, 1980). If this type of compound could be made to be absorbed by plants (through their leaves) and translocated to regions of invention, it could provide a safe non-toxic fungicide and microbicide.

SUMMARY OF THE INVENTION

Although sodium dithionite is not absorbed through leaves of plants, it is systemically absorbable through roots of plants at high concentrations (above 5,000 ppm). Unfortunately, sodium dithionite is easily oxidized by air. When reacted with aldehyde, however, it forms an alkali-metal hydroxyalkyl sulfinate, which is more stable against oxidation. In addition, introduction of an alkyl group into the dithionite molecule makes the resulting compounds absorbable though plant leaves, permitting translocation to regions of infection.

An object of the invention is to provide a safe and non-toxic microbicide, which is useful for application to plants. A further object of the invention is to provide such a microbicide which acts systemically on the plants, preferably when applied to leaves of a plant. A still further object of the invention is to provide a microbicide which is stable against oxidation. These and other objects of the invention are achieved in the manner explained hereinafter.

Although sodium dithionite is an effective microbicide which can be applied to and absorbed through roots of plants at high concentrations (e.g., about 5,000 ppm) or can be applied to a cut stem of an infected plant, it is not systemically absorbable through plant leaves. It is also easily oxidized by air.

By introducing an alkyl group into the dithionite molecule, alkali-metal hydroxyalkyl sulfinates, which are far more stable to oxidation, are prepared The compounds are absorbable through plant leaves and permit translocation to regions of microbe (fungus and/or bacterium) infection. Alkali-metal (preferably sodium) hydroxyalkyl sulfinates e.g. formaldehyde sodium sulfoxylate and acetaldehyde sodium sulfoxylate, are effective microbicides which act systemically when applied to plant leaves.

DETAILS

*Fusarium oxysporum* is a fungus which infects carnation plants. Moreover, this fungus is characterized by its penetrating a plant through its roots, locating in the stem and, on propagation, stopping the flow of liquids and nutrients between roots and leaves, eventually killing the plant. Sodium dithionite, which is incapable of being absorbed through plant leaves, can be absorbed through the roots in high concentrations. If an infected stem is cut, it can absorb the dithionite, effectively destroying the Fusarium. This is useful when cuttings are to be propagated, and their source is uncertain.

Unfortunately, sodium dithionite is easily oxidized by air. When reacted with aldehyde, however, it forms an alkali-metal hydroxyalkyl sulfinate, which is more stable against oxidation. In addition, introduction of an alkyl group into the dithionite molecule produces a compound which is absorbable through plant leaves, permitting translocation to other regions of plant infection.

The absorbability of an alkali-metal (preferably sodium) hydroxyalkyl sulfinate increases with increased molecular weight of the alkyl group, whereas its microbicidal effect decreases with increased molecular weight of the alkyl group.

The absorption rate of formaldehyde sodium sulfoxylate is such that immersing rooted cuttings of carnation plants infected with *Fusarium oxysporum* in a solution of 5,000 ppm of formaldehyde sodium sulfoxylate is sufficient to destroy all fungi. Moreover, the plants recover completely. This is essential when buying cuttings from unreliable sources.

Aldehyde sulfoxylates are well known, as is their method of preparation. Crystallization of a solution of a simple stoichiometric mixture of an aldehyde and sodium dithionite is sufficient. Other sulfoxylates are produced by co-precipitation of sodium aldehyde sulfoxylate with a desirable soluble salt.

This invention is not in any way limited to either carnation plants or *Fusarium oxysporum*. Shigatoka fungi are pests in banana and plantain plantations. Aqueous compositions containing 2,000 ppm of sodium formaldehyde sulfoxylate are effectively applied at a rate of 1 liter of solution per hectare to banana plants infected with Shigatoka fungi. No phytotoxicity is observed. Even after daily application over a period of 45 days, no change is observed during 2 crops on character of flowers, leaves or fruit. Since the oxidation products of aldehyde sulfoxylates are carbon dioxide and sodium sulfate, the products and their degradation products are innocuous to humans, animals and plants.

Aldehyde sulfoxylates have a wide spectrum of effectiveness, not only as a fungicide, but as a bactericide as well. They can even be used to sterilize soil. Unfortunately, by eliminating competing fungi and bacteria in soil, any spores, e.g. of Fusarium, reentering the soil from water or air will increase uncontrollably without competition. It is thus more practical to treat the plant than it is to try to establish sterile conditions.

Aldehyde sulfoxylates are capable of reducing copper salts to copper. When a solution of a copper salt is added to an aldehyde sulfoxylate solution, copper is precipitated in a fine suspension. If this suspension is sprayed on plant leaves, the copper will remain on the surface of the leaves and, on oxidation, will inhibit the germination of fungi spores or conidia.

An effective composition is prepared by mixing 400 grams of sodium formaldehyde sulfoxylate with 23 grams of copper sulfate pentahydrate and enough water to make up 1 liter. The resulting aqueous suspension (diluted 200 times with water and applied by spraying) covers one hectare. Fewer applications of such a composition are required for banana crops as the copper delays reinfection by spores-conidia carried by wind.

The invention and its advantages will be understood from the preceding description. It is apparent that various changes may be made in the process and compositions without departing from the spirit and scope of the invention of sacrificing its material advantages. The process and compositions hereinbefore described are merely illustrative of preferred embodiments of the invention.

What is claimed is:

1. A method of using an alkali-metal dithionate or an alkali metal aldehyde sulfoxylate as a systemic microbicide and which comprises applying an effective amount of the alkali-metal dithionate or of the alkali-metal aldehyde sulfoxylate to a systemically-receptive surface of a fungus- or bacteria-afflicted plant.

2. A method of claim 1 which comprises applying an alkali-metal dithionate to a cut plant surface or to a root of a microbially-infested plant.

3. A method of claim 1 wherein the microbicide is sodium dithinite.

4. A method of claim 1 wherein the microbicide is an aldehyde sulfoxylate.

5. A method of claim 4 wherein the aldehyde sulfoxylate is an alkali metal hydroxyalkyl sulfinate.

6. A method of claim 5 wherein the alkali metal hydroxyalkyl sulfinate is applied to and absorbed through a leaf of the plant.

7. A method of claim 5 wherein the alkali metal hydroxyalkyl sulfinate is formaldehyde sodium sulfoxylate or acetaldehyde sodium sulfoxylate.

8. An agrochemical microbicidal composition which is absorbable through plate leaves and which comprises a microbicidally effective amount of an alkali-metal hydroxyalkyl sulfinate and an agriculturally-compatible carrier in a solution in which an effective amount of copper particles is finely suspended.

9. A composition of claim 8 wherein the alkali-metal hydroxyalkyl sulfinate is formaldehyde sodium sulfoxylate or acetaldehyde sodium sulfoxylate.

* * * * *